United States Patent [19]

Bettman et al.

[11] Patent Number: 5,622,723
[45] Date of Patent: Apr. 22, 1997

[54] PROCEDURE FOR ENCAPSULATING CHLORPHENIRAMINE

[75] Inventors: Marie J. Bettman, Dayton; Sambasiva R. Ghanta, Centerville, both of Ohio

[73] Assignee: Eurand America, Incorporated, Vandalia, Ohio

[21] Appl. No.: 383,033

[22] Filed: Feb. 3, 1995

[51] Int. Cl.⁶ .............................. A61K 9/16; A61K 9/50; B01J 13/02; B01J 13/04
[52] U.S. Cl. .................. 424/495; 424/490; 424/493; 424/494; 424/501; 264/4.1; 264/4.33; 264/4.7; 427/213.3; 427/213.34; 427/213.36; 514/279; 514/299; 514/357; 514/963; 514/974
[58] Field of Search .................... 424/490, 493, 424/494, 495, 501; 427/213.3, 213.34, 213.36; 264/4.1, 4.33, 4.7; 514/279, 299, 357, 963, 974; 546/112, 300, 329, 333, 346

[56] References Cited

U.S. PATENT DOCUMENTS

| | | | |
|---|---|---|---|
| 3,860,733 | 1/1975 | Morse et al. | 426/302 |
| 3,872,227 | 3/1975 | Hoff et al. | 424/271 |
| 4,411,933 | 10/1983 | Samejima et al. | 427/213.3 |
| 5,084,278 | 1/1992 | Mehta | 424/441 |
| 5,407,609 | 4/1995 | Tice et al. | 264/46 |

*Primary Examiner*—Nathan M. Nutter
*Attorney, Agent, or Firm*—John W. Routh

[57] ABSTRACT

An improvement in the process of coacervation of chlorpheniramine maleate is provided whereby a predetermined amount of chlorpheniramine maleate charged to the process is maintained in the microcapsules by pre-saturating the coacervation medium with chlorpheniramine maleate.

8 Claims, No Drawings

PROCEDURE FOR ENCAPSULATING CHLORPHENIRAMINE

BRIEF DESCRIPTION OF THE INVENTION

The present invention is directed to a process for the preparation of individual taste masked microcapsules containing a predetermined amount of chlorpheniramine maleate. More particularly the present invention is directed to a process for the preparation of individual taste masked microcapsules containing a predetermined amount of chlorpheniramine maleate by microencapsulating the chlorpheniramine maleate in a heated coacervation medium including cyclohexane, an encapsulating polymer and a phase inducing polymer and subsequently cooling the coacervation medium. In the process of the present invention, an excess of chlorpheniramine maleate above the predetermined amount is charged to the coacervation medium in an amount sufficient to saturate the cyclohexane in the coacervation medium.

BACKGROUND OF THE INVENTION

The process for the preparation of individual taste masked bitter tasting pharmaceuticals by microencapsulation of the pharmaceutical in a coacervation medium including cyclohexane, an encapsulating polymer and a phase inducing agent is well known in the art. A typical process is described in U.S. Pat. No. 3,860,733 to Lewis D. Morse et al. which discloses microencapsulation of vitamin mixes by polymer/polymer incompatibility coacervation. A disclosed coating polymer is ethylcellulose, a disclosed phase inducing polymer is polyethylene and a disclosed solvent for the polymers is cyclohexane. Because of its detailed description of the coacervation process, U.S. Pat. No. 3,860,733 is incorporated herein by reference in its entirety. Another description of the preparation of ethylcellulose coated microcapsules by the liquid-liquid phase separation of ethylcellulose in cyclohexane is given in U.S. Pat. No. 4,411,933, which patent disclosure is also incorporated by reference herein in its entirety. U.S. Pat. No. 4,411,933 further states that the core material to be microencapsulated should be insoluble or incompatible in cyclohexane or a cyclohexane solution containing either one or both of the coating polymer and phase inducing polymer.

SUMMARY OF THE INVENTION

According to this invention, a method is provided wherein a core material such as chlorpheniramine maleate, which is somewhat soluble in cyclohexane, can be encapsulated in a predetermined amount with respect to the coating polymer and/or in a predetermined amount with respect to a different pharmaceutical, such as pseudoephedrine hydrochloride, in admixture with the chlorpheniramine maleate, in order to maintain a definite ratio of chlorpheniramine maleate to pseudoephedrine hydrochloride. The encapsulation of the predetermined amount of chlorpheniramine maleate is accomplished by first charging to the coacervation medium an excess of chlorpheniramine maleate above the predetermined amount sufficient to saturate the cyclohexane and/or the coacervation medium with chlorpheniramine maleate. After settling of the microcapsules the coacervation medium is decanted and/or filtered and the microcapsules may optionally be washed with additional cyclohexane. The remaining cyclohexane saturated with chlorpheniramine maleate can be recycled for use in processing the next batch. Alternatively, the dissolved chlorpheniramine maleate can be separated from the cyclohexane and recovered.

DETAILED DESCRIPTION OF THE INVENTION

In the process of the invention, the preferred coacervation medium includes cyclohexane alone or in admixture with hexane. Cyclohexane when saturated with chlorpheniramine maleate at 80° C. contains 148.8 micrograms of chlorpheniramine maleate per milliliter of cyclohexane. Analytical testing has shown that there is no degradation of chlorpheniramine maleate in the cyclohexane so that recycling of the saturated cyclohexane is possible. Preferably the chlorpheniramine maleate saturation of the cyclohexane is accomplished before the encapsulation process begins.

The chlorpheniramine maleate to be encapsulated can be added to the pretreated cyclohexane alone or in conjunction with another pharmaceutical material, such as pseudoephedrine hydrochloride, with which it is commonly administered in a combined dosage form. Preferably a mixture of the chlorpheniramine maleate and the other pharmaceutical material are granulated to form a drug combination having defined proportions of each ingredient for a suitable dosage form. For example, for a children's dosage form the proportions can be 7.5 milligrams of pseudoephedrine hydrochloride and 0.5 milligrams of chlorpheniramine maleate. Accordingly the drug ratio in the granular material and in the encapsulated granules would be 7.5 to 0.5.

The ethylcellulose suitable for use as the encapsulating polymer can be any of the commercial types customarily used for encapsulating purposes. A typical ethylcellulose has a 45 to 50 per cent ethoxyl content and a 95–110 cps viscosity. The amount of ethylcellulose employed can vary but for taste masking purposes, the ethylcellulose should comprise about 25% to 35% by weight of the coated granules. The ethylcellulose used in the following examples was Ethylcellulose, NF manufactured by Dow Chemical Company having a 49.4 per cent ethoxyl content and a 103.6 cps viscosity.

The polyethylene suitable for use as the phase inducer can have a molecular weight of between 5,000 and 10,000 and can be any of the commercial types customarily used for encapsulating purposes. The amount of polyethylene employed depends somewhat on the type employed but the amount should usually provide a ratio to the ethylcellulose of about 4:1 to about 8:1 parts by weight of ethylcellulose per part by weight of polyethylene. The brand of polyethylene used in the following examples was Epolene C-10, manufactured by Eastman Kodak Company, viscosity at 150° C. of 8175 cps within the range of 7000–11000 cps and a softening point of 101.6° C. within the range of 95°–110° C.

The process of the invention is now described below with reference to the specific examples.

EXAMPLE 1

This example illustrates the use of the process of the invention to provide taste masked encapsulated granules of chlorpheniramine maleate and pseudoephedrine hydrochloride for incorporation into children's tablets.

The granules containing the raw drug were prepared by first preparing a mixture containing 33.4–36.9% by weight of pseudoephedrine hydrochloride, 2.23–2.46% by weight of chlorpheniramine maleate and the remainder being microcrystalline cellulose. Because of the required low combination dosage level of the drugs the inert carrier was used to achieve acceptable dose level uniformity. The granulation was accomplished in this instance in a top spray fluid bed unit. The granules had a typical particle size range as shown below.

| US Std. Sieve # | % Retained |
| --- | --- |
| 14 | — |
| 30 | — |
| 40 | 1.1 |
| 60 | 3.4 |
| 100 | 31.8 |
| 140 | 36.6 |
| thru 140 | — |
| 200 | 18.3 |
| 270 | 6.3 |
| Pan | 2.5 |
|  | 100.0% |

The granules may be prepared by other granulation techniques known to the art such as wet granulation. See for example U.S. Pat. Nos. 5,084,278 and 3,872,227.

The proportions of ingredients used in this example were as follows:

| Cyclohexane | 1000 grams |
| --- | --- |
| Polyethylene C-10 | 5 grams |
| Ethylcellulose NF | 30 grams |
| Granules | 90 grams |
| Chlorpheniramine Maleate, USP | 192 milligrams |

Into a two liter glass beaker equipped with a 4 inch turbine and a switch blade baffle were placed the 1000 grams of cyclohexane together with 192 milligrams of chlorpheniramine maleate. The batch was heated to 80° C. with 250 rpm agitation using a heating mantle and an aluminum foil cover. The mixture was cooled to 35° C. The remaining ingredients were then added and the mixture was heated to 80° C. with 250 rpm agitation and use of the aluminum cover. Once the temperature of the mixture reached 80° C., the heat source was removed and the mixture was allowed to cool slowly to 35° C. with 300 rpm agitation. At 35° C. the contents of the beaker were decanted into a Buchner filter with no washing and tray dried overnight. The microcapsules were sieved and a typical analysis is shown below in the second column of the table.

In another experiment, the ingredient amount and operating conditions were the same as in Example 1 except that the granule content was 60 grams and the ethylcellulose content was 20 grams providing a phase ratio of 3:1 but an ethylcellulose concentration of 2%. The sieve analysis is shown in the third column of the table below.

In a further experiment the ingredient amount and operating conditions were the same as in Example 1 except that the granule content was 120 grams and the ethylcellulose content was 40 grams providing a phase ratio of 3:1 but an ethylcellulose concentration of 4%. The sieve analysis is shown in the fourth column of the table below.

| Particle Size Analysis | | % Retained | | |
| --- | --- | --- | --- | --- |
| US Std. Mesh | 40 | 28.8 | 23.8 | 14.3 |
|  | 60 | 17.9 | 26.5 | 26.1 |
|  | 100 | 35.0 | 37.0 | 40.1 |
|  | 170 | 15.6 | 10.6 | 16.4 |
|  | 200 | 1.8 | 1.1 | 2.1 |
|  | 270 | 0.8 | 0.6 | 0.8 |
|  | Pan | 0.1 | 0.4 | 0.2 |
|  |  | 100.0% | 100.0% | 100.0% |

The product of Example 1 had an acceptable taste masking of the bitter taste of the pharmaceutical ingredients and had a good mouth feel. The product was of an appropriate particle size and met an acceptable release for in vitro requirements. Process variables for the pseudoephedrine hydrochloride-chlorpheniramine maleate combination for taste masking purposes are a phase ratio of 2:1 through 4:1 parts by weight of granules per part by weight of ethylcellulose, a 2% through 4% concentration of ethylcellulose in cyclohexane, and a 0.4 through 0.65% concentration of polyethylene in cyclohexane. Operation variables include sufficient agitation to keep the microcapsules suspended in the coacervation medium during and after their formation and a temperature range including a maximum temperature of about 80° C. and a minimum temperature of about 30°–35° C. Chlorpheniramine maleate should be heated with the cyclohexane as a first step to saturate the cyclohexane and the other ingredients can be added following standard microencapsulating procedure at a temperature sufficiently high to dissolve the ethylcellulose and the polyethylene.

Optimum values for the process variables are a phase ratio of 3:1, a 3% concentration of ethylcellulose in cyclohexane, a 0.5% concentration of polyethylene in cyclohexane, and a total solids concentration of 12.5% in cyclohexane to provide 25% by weight ethylcellulose coated granules.

With respect to recycling the coacervation medium, cyclohexane containing dissolved chlorpheniramine maleate was tested for possible degradation of chlorpheniramine maleate in this solvent. After five cycles of heating to 80° C. and cooling to 35° C., no evidence of drug degradation was determined.

We claim:

1. In a process for microencapsulating a predetermined amount of finely divided chlorpheniramine maleate in a heated then cooled coacervation medium including cyclohexane, an encapsulating polymer and a phase inducing polymer, and separating the microcapsules containing chlorpheniramine maleate, the improvement which comprises charging an excess of chlorpheniramine maleate to the coacervation medium sufficient to saturate the cyclohexane in the heated coacervation medium with chlorpheniramine maleate and separating the microcapsules containing the predetermined amount of chlorpheniramine maleate from the coacervation medium.

2. The process of claim 1 wherein the encapsulating polymer is ethylcellulose and the phase inducing polymer is polyethylene.

3. A process for microencapsulating a granulated admixture comprising in predetermined proportions chlorpheniramine maleate and pseudoephedrine hydrochloride in a heated then cooled coacervation medium including cyclohexane as the solvent, ethylcellulose as the encapsulating polymer and polyethylene as the phase inducing polymer, the said process including the steps of:

a) charging chlorpheniramine maleate to the coacervation medium sufficient to saturate the cyclohexane in the heated coacervation medium with chlorpheniramine maleate, b) forming individual microcapsules of ethylcellulose coated granules of the granulated admixture of chlorpheniramine maleate and pseudoephedrine hydrochloride, and c) separating individual microcapsules of the said ethylcellulose coated granules containing approximately the same predetermined proportions as in the uncoated granules charged to the process of chlorpheniramine maleate and pseudoephedrine hydrochloride.

4. The process of claim 3 wherein the coacervation medium is heated to about 80° C. then cooled to about 30° C.–35° C. during the microencapsulating process, the ethylcellulose concentration in the cyclohexane is about 2% to 4% by weight, the polyethylene concentration in the cyclohexane is about 0.4% to about 0.65% by weight, and the ratio of part by weight of the granulated admixture to parts by weight of ethylcellulose is about 2:1 to about 4:1.

5. The taste masked product of claim 4.

6. A process for microencapsulating a predetermined amount of finely divided chlorpheniramine maleate in a heated then cooled coacervation medium containing cyclohexane which comprises charging to the heated coacervation medium sufficient chlorpheniramine maleate to saturate the cyclohexane content of the coacervation medium, charging the predetermined amount of chlorpheniramine maleate to the coacervation medium, charging to the coacervation medium an encapsulating polymer and a phase inducing polymer, cooling the coacervation medium and separating the microcapsules containing the predetermined amount of chlorpheniramine maleate from the cooled coacervation medium.

7. The process of claim 6 wherein the coacervation medium is recycled after separation of the microcapsules containing the predetermined amount of chlorpheniramine maleate.

8. The process of claim 3 wherein the coacervation medium is recycled to step a) of claim 3 after separation of the microcapsules containing the predetermined amount of chlorpheniramine maleate.

* * * * *